US006817995B1

(12) United States Patent
Halpern

(10) Patent No.: US 6,817,995 B1
(45) Date of Patent: Nov. 16, 2004

(54) REINFORCED CATHETER CONNECTOR AND SYSTEM

(75) Inventor: David Halpern, Alpharetta, GA (US)

(73) Assignee: Isotron ,Inc., Alpharetta, GA (US)

( * ) Notice: Subject to any disclaimer, the term of this patent is extended or adjusted under 35 U.S.C. 154(b) by 0 days.

(21) Appl. No.: 09/553,743

(22) Filed: Apr. 20, 2000

(51) Int. Cl.[7] .............................................. A61M 25/00
(52) U.S. Cl. ...................... 604/524; 604/523; 604/527
(58) Field of Search ................................ 604/524, 523, 604/526, 527, 93.01, 103.1, 264

(56) References Cited

U.S. PATENT DOCUMENTS

| | | | |
|---|---|---|---|
| 4,112,306 A | | 9/1978 | Nunan ......................... 250/499 |
| 4,150,298 A | | 4/1979 | Brault et al. ................. 250/497 |
| 4,197,170 A | | 4/1980 | Malson et al. ............... 204/1.5 |
| 4,469,483 A | * | 9/1984 | Becker et al. ............... 604/280 |

(List continued on next page.)

OTHER PUBLICATIONS

Rolf. F. Barth, et al., "Boron Neutron Capture Therapy for Cancer", Scientific American, Oct. 1990, pp. 100–107.
R. C. Martin et al., "Development of High–activity $^{252}$Cf Sources for Neutron Brachytherapy", Appl. Radiat. Isot., vol. 48, pp. 1567–1570, 1997.

(List continued on next page.)

Primary Examiner—Christopher L. Chin
Assistant Examiner—Ann Y Lam

(74) Attorney, Agent, or Firm—Gray Cary Ware & Freidenrich LLP

(57) ABSTRACT

In accordance with the invention, A reinforced catheter is provided comprising an inner layer forming a catheter body, the body having a distal end and a proximal end, the distal end having a closed tip end, a middle reinforcing layer extending over the first inner layer to the distal end and an outer layer extending over the middle reinforcing layer. Additionally, a connector for coupling a catheter to an extension tube or afterloader is provided comprising a first half having a housing with at least one pair of opposing cutout portions of a first depth provided thereon, a second half slidably connectable with the first half and a biasing means for securing the second half within the housing. Additionally, a catheter system is provided comprising a reinforced catheter, including an inner layer forming a catheter body, the body having a distal end and a proximal end, the distal end having a closed tip end, a middle reinforcing layer extending over the first inner layer to the distal end and an outer layer extending over the middle reinforcing layer and a connector for coupling a catheter to an extension tube or afterloader, the connector including a first half having a housing with at least one pair of opposing cutout portions of a first depth provided thereon, a second half slidably connectable with the first half and a biasing means for securing the second half within the housing. A method for performing a surgical procedure on a patient is also provided comprising inserting a reinforced catheter into the body of the patient, the reinforced catheter including an inner layer forming a catheter body, the body having a distal end and a proximal end, the distal end having a closed tip end, a middle reinforcing layer extending over the first inner layer to the distal end and an outer layer extending over the middle reinforcing layer.

4 Claims, 8 Drawing Sheets

U.S. PATENT DOCUMENTS

| | | | |
|---|---|---|---|
| 4,508,119 A | | 4/1985 | Tukamoto ............... 128/329 A |
| 4,510,924 A | | 4/1985 | Gray ......................... 128/1.2 |
| 4,563,180 A | * | 1/1986 | Jervis et al. ................. 604/280 |
| 4,760,266 A | | 7/1988 | Schulz ..................... 250/493.1 |
| 4,763,642 A | | 8/1988 | Horowitz .................... 128/1.2 |
| 4,819,618 A | | 4/1989 | Liprie ........................... 600/7 |
| 4,851,694 A | | 7/1989 | Rague et al. ............ 250/497.1 |
| 4,853,550 A | | 8/1989 | Schulz ..................... 250/493.1 |
| H669 H | | 9/1989 | Fairchild et al. ............... 600/3 |
| 4,891,165 A | | 1/1990 | Suthanthiran ............... 252/633 |
| 4,897,076 A | | 1/1990 | Puthawala et al. ............. 600/7 |
| 4,957,476 A | | 9/1990 | Cano ............................ 600/7 |
| 4,963,128 A | | 10/1990 | Daniel et al. .................. 600/7 |
| 4,994,013 A | | 2/1991 | Suthanthiran et al. ......... 600/8 |
| 5,057,092 A | * | 10/1991 | Webster, Jr. ................. 604/282 |
| 5,084,002 A | | 1/1992 | Liprie ........................... 600/7 |
| 5,092,834 A | | 3/1992 | Bradshaw et al. ............. 600/7 |
| 5,139,473 A | | 8/1992 | Bradshaw et al. ............. 600/3 |
| 5,141,487 A | | 8/1992 | Liprie ........................... 600/7 |
| 5,183,455 A | | 2/1993 | Hayman et al. ............... 600/7 |
| 5,199,939 A | | 4/1993 | Dake et al. .................... 600/3 |
| 5,267,960 A | | 12/1993 | Hayman et al. ............ 604/106 |
| 5,282,781 A | | 2/1994 | Liprie ........................... 600/3 |
| 5,317,616 A | | 5/1994 | Swerdloff et al. ............ 378/65 |
| 5,322,499 A | | 6/1994 | Liprie ........................... 600/8 |
| 5,342,283 A | | 8/1994 | Good ............................ 600/8 |
| 5,364,336 A | | 11/1994 | Carr ............................. 600/2 |
| 5,395,300 A | | 3/1995 | Liprie ........................... 600/3 |
| 5,498,227 A | | 3/1996 | Mawad ......................... 600/3 |
| 5,503,614 A | | 4/1996 | Liprie ........................... 600/7 |
| 5,531,662 A | | 7/1996 | Carr ............................. 600/2 |
| 5,562,594 A | | 10/1996 | Weeks .......................... 600/3 |
| 5,575,749 A | | 11/1996 | Liprie ........................... 600/3 |
| 5,599,796 A | | 2/1997 | Schinazi et al. ............. 514/44 |
| 5,603,694 A | * | 2/1997 | Brown et al. ................. 604/49 |
| 5,616,114 A | | 4/1997 | Thornton et al. .............. 600/3 |
| 5,618,266 A | | 4/1997 | Liprie ........................ 604/21 |
| 5,624,372 A | | 4/1997 | Liprie ........................... 600/3 |
| 5,643,171 A | | 7/1997 | Bradshaw et al. ............. 600/1 |
| 5,662,580 A | | 9/1997 | Bradshaw et al. ............. 600/3 |
| 5,713,828 A | | 2/1998 | Coniglione .................... 600/7 |
| 5,720,717 A | | 2/1998 | D'Andrea ..................... 604/21 |
| 5,722,985 A | | 3/1998 | Pettus ........................ 606/180 |
| 5,782,741 A | | 7/1998 | Bradshaw et al. ............. 600/3 |
| 5,782,811 A | * | 7/1998 | Samson et al. ............. 604/282 |
| 5,788,713 A | | 8/1998 | Dubach et al. ............. 606/130 |
| 5,800,333 A | | 9/1998 | Liprie ........................... 600/3 |
| 5,803,895 A | | 9/1998 | Kronholz et al. .............. 600/3 |
| 5,807,231 A | | 9/1998 | Liprie ........................... 600/3 |
| 5,833,593 A | | 11/1998 | Liprie ........................... 600/3 |
| 5,840,008 A | | 11/1998 | Klein et al. .................... 600/3 |
| 5,851,172 A | | 12/1998 | Bueche et al. ................. 600/7 |
| 5,857,956 A | | 1/1999 | Liprie ........................... 600/7 |
| 5,860,909 A | | 1/1999 | Mich et al. .................... 600/7 |
| 5,863,284 A | | 1/1999 | Klein ............................ 600/3 |
| 5,866,127 A | | 2/1999 | Senger et al. ............ 424/178.1 |
| 5,868,757 A | | 2/1999 | Koutrouvelis ............... 606/130 |
| 5,872,107 A | | 2/1999 | Schinazi et al. ............. 514/44 |
| 5,882,291 A | | 3/1999 | Bradshaw et al. ............. 600/3 |
| 6,045,734 A | * | 4/2000 | Luther et al. ............... 264/103 |
| 6,053,900 A | * | 4/2000 | Brown et al. ............... 604/500 |

OTHER PUBLICATIONS

Yosh Maruyama, M.D., FACR, et al., "Californium–252 Neutron Brachytherapy", From Nag S (ed): Principles and Practice of Brachytherapy, pp. 649–687, 1997.

R.A. Patchell, M.D., et al., "A phase I trial of neturon brachytherapy for the treatment of malignant gliomas", The British Journal of Radiology, 70, pp. 1162–1168, 1997.

Yosh Maruyama, M.D., FACR, et al., "Study of Biological Effects of Varying Mixtures of CF–252 and Gamma Radiation on the Acute Radiation Syndromes: Relevance to Clinical Radiotherapy of Radioresistant Cancer", I. J. Radiation Oncology, Biology, Physics, vol. 27, No. 4, pp. 907–914, 1993.

J.C. Yanch, et al., "Dosimetry of $^{252}$Cf Sources for Neutron Radiotherapy with and without Augmentation by Boron Neutron Capture Therapy", Radiation Research, 131, pp. 249–256, 1992.

Roy A. Patchell, M.D., et al., "Postoperative Radiotherapy in the Treatment of Single Metastases to the Brain," JAMA, vol. 280, No. 17, pp. 1485–1489, Nov. 1998.

Jeffrey A. Coderr, et al., Review, "The Radiation Biology of Boron Neutron Capture Therapy", Radiation Research, 151, pp. 1–18, 1999.

Darrel D. Joel., "Effect of dose and infusion time on the delivery of p–boronophenylalanine for neutron capture therapy", Journal of Neuro–Oncology 41, pp. 213–221, 1999.

J.G. Wierzbicki, et al., Measurement of augmentation of $^{252}$Cf implant by $^{10}$B and $^{157}$Gd neutron capture, Med. Phys., 21(6), pp. 787–790, Jun. 1994.

Patrick J. Kelly, M.D., "Computer–Directed Stereotactic Resection of Brain Tumors", Neurosurgical Operative Atlas, vol. 1 (4), pp. 299–313, 1991.

Setti S. Rengachary, M.D., "Frontal Lobectomy", Neurosurgical Operative Atllas, vol. 3, pp. 175–183, 1993.

Raymond D. Adams, M.A., M.D., et al., "The Major Categories of Neurologic Disease", Principles of Neurology, Part IV, CH. 30, pp. 446–455, 1981.

Jeffrey D. MacDonald, M.D. Ph.D., et al., "Interstitial Brachytherapy", Neurosurgical Operative Atlas, vol. 2(2), pp. 143–151, 1992.

* cited by examiner

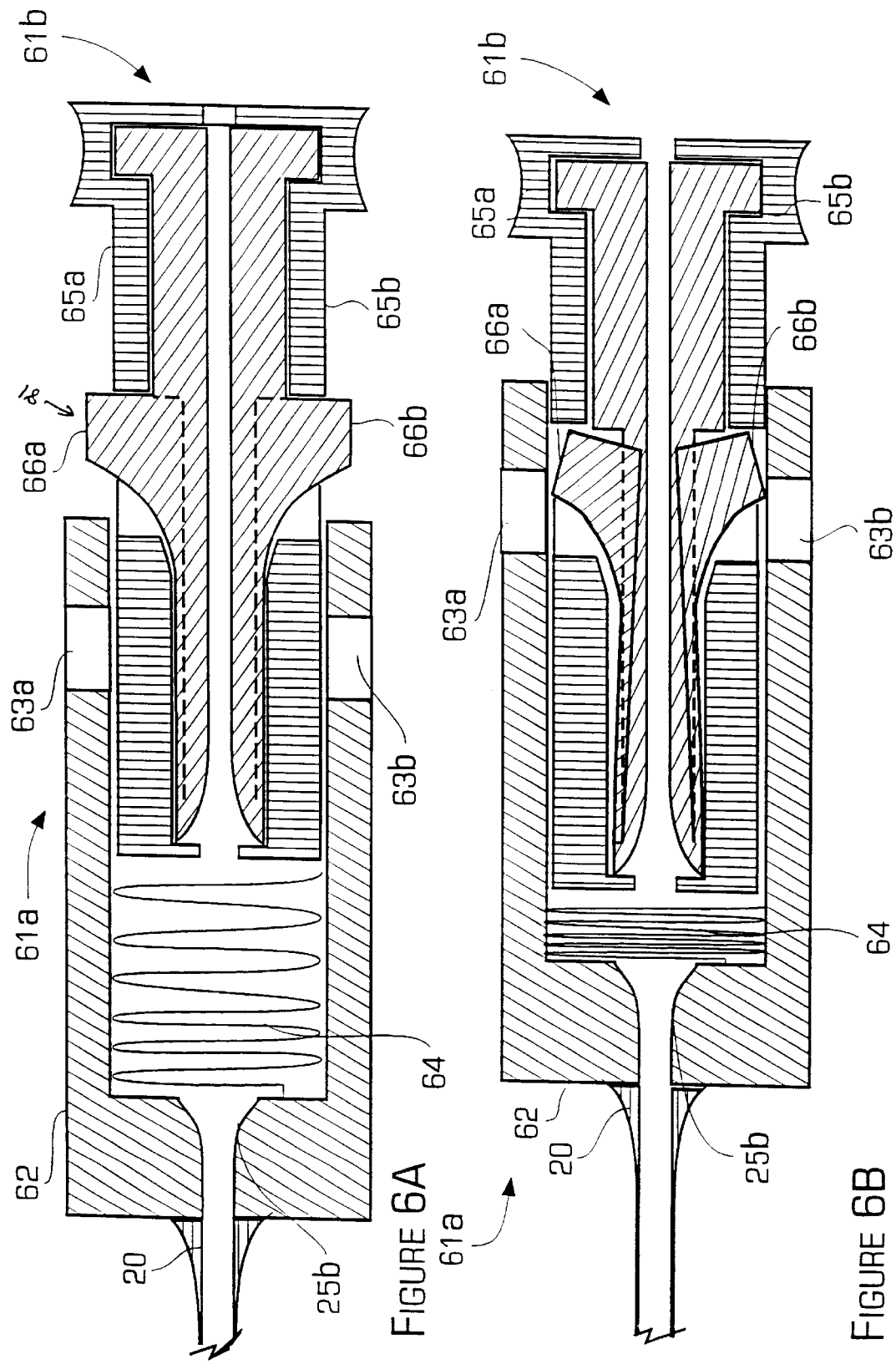

REINFORCED CATHETER CONNECTOR AND SYSTEM

The present invention relates generally to catheters for radiation therapy and to connectors and systems for use with such catheters.

BACKGROUND OF THE INVENTION

Loss of normal control of cellular proliferation results in unregulated cell growth and, often, the formation of cellular masses commonly known as tumors. Tumors may be malignant or non-malignant. The cells of malignant tumors often exhibit a lack of normal differentiation and possess the ability to invade local tissues and metastasize, whereas, in non-malignant tumors, the mass of cells is generally localized. Malignant tumors can develop in any organ at any age and, even with treatment, often result in the death of the subject. While not typically posing a threat to life, non-malignant tumors can impose severe restrictions on normal physiological function.

Tumors are typically treated by surgical removal, radiation, and/or chemotherapy. Surgery is the oldest effective form of tumor therapy and can often result in a complete cure, depending on the type and nature of the tumor. Many tumors, however, occur in locations and/or number that make surgery impossible or impractical. Also, surgical debulking (the removal of the tumor) is not guaranteed to remove all abnormal cells, particularly in the case of tumors located in the brain where maximum preservation of normal tissue is desired. These abnormal cells remaining after surgery pose an increased risk of tumor re-growth and/or metastasis.

Radiation therapy is often used as an adjunct to surgery. Various types of radiation, both from external and implanted sources, have been used with some success. Low linear-energy-transfer (LET) sources, such as beta particles and gamma rays, require the presence of oxygen for their pharmacologic activity. Many tumors, however, are hypoxic (have reduced oxygen content) due to reduced collateral blood vessel growth into the tumor interstitia, limiting the effectiveness of low LET sources and requiring repeated treatments over extended periods of time to produce any significant reduction in tumor cells.

Brachytherapy using an implantable neutron emitting source has been used as an alternative to external radiation beams. Most of the neutron-emitting isotopes are unsuitable for brachytherapy, however, because of short half-lives or low specific neutron emission rates (i.e. neutrons per sec per gram). The transplutonium radioactive isotope californium-252 ($^{252}$Cf) is an exception because it has a fairly long half-life of 2.6 years and a specific neutron emission rate of $2.34 \times 10^{12}$ neutrons per sec per gram. The neutrons emitted from $^{252}$Cf have an average energy of 2.3 MeV, which is a high LET and proven to be effective against hypoxic tumors. Brachytherapy techniques are described in detail in Applicant's co-pending U.S. patent application Ser. No. 09/394,234, entitled "Methods for Treating Solid Tumors Using Neutron Therapy," filed Sep. 13, 1999 and in U.S. patent application Ser. No. 09/395,324, entitled "Neutron Brachytherapy Device and Method," filed Sep. 13, 1999, in the name of Applicant and another inventor, which are both incorporated herein by reference.

Generally, conventional thin wall tubing catheters can be utilized in the brachytherapy process, but are not desirable because the thin wall tubing of the catheters may become kinked due to handling and may even collapse during usage. Kinks reduce the effectiveness of the therapy because the radiation source may become trapped within the patient so that the patient receives an unwanted dose of radiation. Further, metal reinforced catheters cannot generally be utilized in brachytherapy techniques since the metal layers normally attenuate the conventional radiation (i.e. x-ray, gamma and beta).

Additionally, conventional catheter designs utilize a connector to couple the catheter to the afterloader. One such connector is a tapered Leur connector. The Leur connector couples to its mating part via a clockwise/counterclockwise rotating relationship. However, this rotating relationship is undesirable because the catheter may change positions while inserted in a patient's body or could become disengaged by the rotation necessary to lock the catheter to the connector.

Accordingly, there is a need in the art for catheters that can be used for brachytherapy and other medical procedures that reduce the occurrence of collapse and kinking during usage. It is to these ends that the present invention is directed.

SUMMARY OF THE INVENTION

In accordance with the invention, A reinforced catheter is provided comprising an inner layer forming a catheter body, the body having a distal end and a proximal end, the distal end having a closed tip end, a middle reinforcing layer extending over the first inner layer to the distal end and an outer layer extending over the middle reinforcing layer.

In an alternative embodiment, a reinforced catheter is provided comprising an inner layer forming a catheter body, the body having a distal end and a proximal end, the distal end having a closed tip end, a middle reinforcing layer extending over the first inner layer to the distal end, the middle reinforcing layer cooperating with the inner layer to reduce the kinking of the inner layer and an outer layer extending over the middle reinforcing layer to seal the reinforced catheter body and to provide a surface coating for the catheter so that the catheter is capable of being easily guided into a patient.

In still another embodiment, a reinforced catheter is provided comprising an inner layer forming a catheter body, the body having a first end and a second end, the first end being closed to form a tip end, a middle reinforcing layer over the inner layer, the middle reinforcing layer extending adjacent to the tip end and an outer layer over the middle reinforcing layer, the outer layer extending to and covering the tip end such that a first portion of the catheter is characterized by a first thickness formed of the inner, middle and outer layers and a second portion of the catheter is characterized by a second thickness formed of the inner and outer layers.

Additionally, a connector for coupling a catheter to an extension tube or afterloader is provided comprising a first half having a housing with at least one pair of opposing cutout portions of a first depth provided thereon, a second half slidably connectable with the first half and a biasing means for securing the second half within the housing.

In an alternative embodiment, a connector for coupling a catheter to an extension tube or afterloader is provided comprising a first half having a housing with at least one pair of opposing cutout portions of a first depth provided thereon and a second half slidably connectable with the first half, the second half having an inner member and an outer member configured to slide relative to the inner member, the inner member having at least one pair of opposing tab portions provided thereon, the tab portions configured to protrude through the outer member such that when the first half and the second half are mated, the tab portions engage the cutout portions in the housing to secure the first half and the second half.

Additionally, a catheter system is provided comprising a reinforced catheter, including an inner layer forming a catheter body, the body having a distal end and a proximal end, the distal end having a closed tip end, a middle reinforcing layer extending over the first inner layer to the distal end and an outer layer extending over the middle reinforcing layer and a connector for coupling a catheter to an extension tube or afterloader, the connector including a first half having a housing with at least one pair of opposing cutout portions of a first depth provided thereon, a second half slidably connectable with the first half and a biasing means for securing the second half within the housing.

Additionally, a catheter system is provided comprising a reinforced catheter having an inner layer forming a catheter body, the body having a first end and a second end, the first end being closed to form a tip end, the tip end configured to house a radiation source; a middle reinforcing layer over said inner layer extending to the tip end; and a third outer layer over the middle reinforcing layer and a connector for coupling the second end to an extension tubing end, the second end being flared to form a funnel shape configured to provide for strain relief and to minimize mismatch of lumens when the catheter body is coupled with the connector, the connector having a first half, the first half having a housing with at least one pair of opposing cutout portions of a first depth provided therein; and a biasing means for securing the second half within the housing such that the biasing means and the second end of the catheter body are concentrically located; and a second half slidably connectable with the first half, the second half having an inner member with at least one pair of opposing tab portions are provided thereon and an outer member configured to slide relative to the inner member, the tab portions configured to protrude through the outer member such that when the first half and the second half are mated, the tab portions engage the cutout portions in the housing to secure the first half and the second half, the tab portions configured to not protrude beyond the first depth of the opposing cutout portions.

A method for performing a surgical procedure on a patient is also provided comprising inserting a reinforced catheter into the body of the patient, the reinforced catheter including an inner layer forming a catheter body, the body having a distal end and a proximal end, the distal end having a closed tip end, a middle reinforcing layer extending over the first inner layer to the distal end and an outer layer extending over the middle reinforcing layer.

Advantageously, kinking in a catheter body will be unlikely to occur as a result of the reinforced catheter body. Also, when mated, the connector will be unlikely to disengage the catheter and extension tubing due to the operation of opposing tab and cutout portions that create a locking mechanism. Therefore, a suitable catheter and connector may be utilized during surgical procedures without endangering a patient.

BRIEF DESCRIPTION OF THE DRAWINGS

FIG. 6A is a diagram of an embodiment of a catheter connector in accordance with the invention showing a slidable connection member being disengaged from a connection housing member;

FIG. 6B is a diagram of the catheter connector of FIG. 6A showing the slidable member being inserted into the connector housing member;

DETAILED DESCRIPTION OF THE PREFERRED EMBODIMENTS

Figure 1:
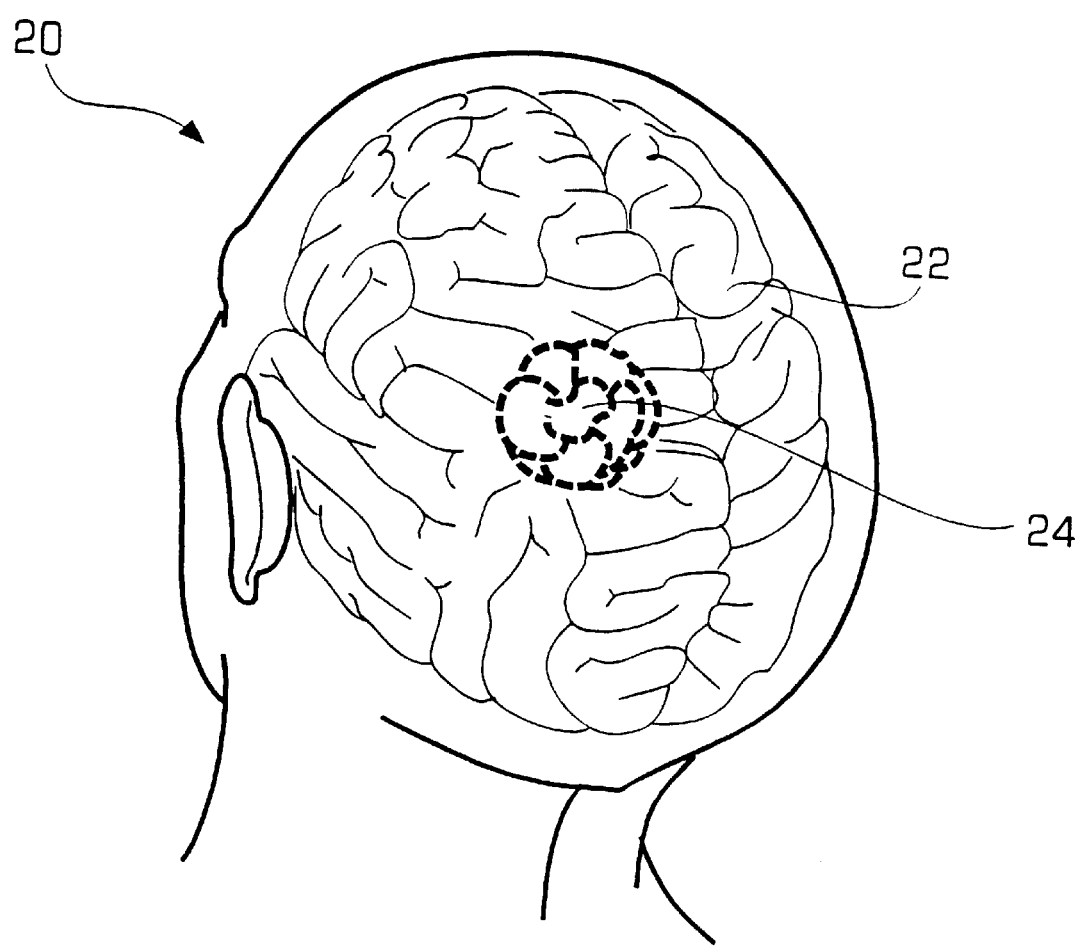
FIG. 1 is a diagram illustrating a patient's head.

FIG. 1 shows a diagram illustrating a patient's head 10. The diagram shows the patient's brain 12 with a deep-seated tumor 14 that may be treated using neutron brachytherapy. In one typical treatment, a surgeon may surgically remove a majority of the tumor, known as tumor debulking. Neutron brachytherapy may then be used to kill the remaining tumor cells (on the periphery of the tumor) instead of a conventional radiation or chemotherapy treatment. Neutron brachytherapy is more effective than the conventional radiation in killing the hypoxic brain tumor cells. It should be noted that while FIG. 1 shows a representation of the human brain, the novel catheters in accordance with the invention can be used in any portion of the human body and the brain is shown merely for illustrative and exemplary purposes.

In order to treat such tumors, a radiation source must be inserted into the tumor 14. A catheter may be utilized to place a neutron source within the tumor 14. The catheters used for radiation treatment in the brain are generally much shorter than catheters used in other areas of the body. In order to couple one of these catheters to an afterloader, extension tubing is used. However, it is also possible that the catheter may be formed integrally with the afterloader. Together, the catheter and extension tubing are similar in length as the catheters used in other areas of the body. However, conventional catheters can suffer the disadvantage of being susceptible to kinking as a result of handling and placement in the body. This disadvantage could be dangerous to a patient since a radiation source could become stuck within the patient subjecting the patient to undesirable neutron irradiation. A reinforced catheter in accordance with the invention that overcomes the disadvantages of the conventional catheters and connectors will now be described.

Figure 2A:
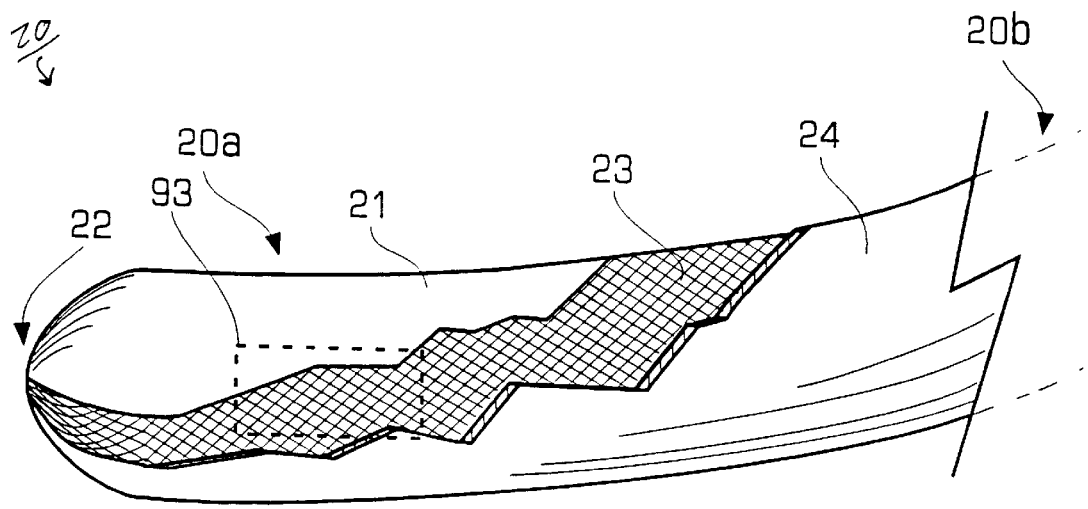
FIGS. 2A and 2B are diagrams of an embodiment of a catheter according to the invention.
Figure 2B:
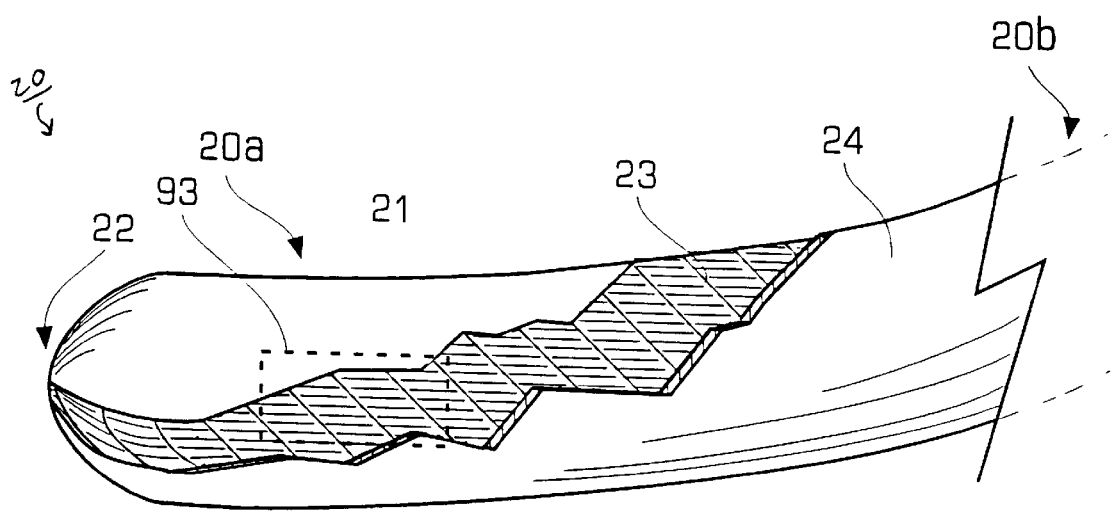

FIGS. 2A and 2B show a diagram of a reinforced catheter 20 in accordance with an embodiment of the invention. The reinforced catheter 20 includes an inner layer 21 to assure unrestricted passage of a radiation source 93. The catheter 20 further includes a middle reinforcing layer 23 over the inner layer 21 for reinforcing the catheter body. The middle layer 23 can be a braided or coiled sheath that provides superior torque and handling characteristics along with providing flexibility and resistance to kinking or compression. The catheter 20 also includes an outer layer 24 applied over the reinforcing layer 23 providing the catheter with a lubricous surface making it easier to advance the catheter in a patient's body.

A distal end 20a of the catheter body 20 may be closed to form a tip end 22. The tip end 22 may be configured to house a radiation source. Radiation sources suitable for brachytherapy and tip end 22 configurations are described in detail in the previously incorporated co-pending U.S. patent application Ser. Nos. 09/394,234 and 09/395,324.

The inner layer 21 of the catheter body 20 may be characterized by a low friction coefficient and may be made of a material with that characteristic such as plastic and is preferably polytetrafluoroethylene. Preferably, the wall thickness of the inner layer 21 may be on the order of 0.002 inches.

The reinforcing cylindrical layer 23 over the inner layer 21 may extend entirely over the inner layer 21 such that it overlays the tip end 22. This reinforcing layer 23 may be made of metallic or non-metallic material, for example a strong metallic, resilient material such as stainless steel, or a non-metallic material such as nylon. The reinforcing layer 23 may be comprised of strands, such as a round wire tightly braided around the inner layer 21 or it may be a rectangular cross-sectional wire tightly coiled around the inner layer 21. In an embodiment of the invention, a cross-section of the wire may measure about 0.004 inches×0.012 inches.

The outer layer 24 seals the catheter body and is preferably of a material that provides a low friction coating so that the catheter can be easily inserted into a patient's body, such as during a surgical procedure, such as brachytherapy. Preferably, the coating may be plastic, polyurethane or nylon. The coating may also be silicone. In an embodiment of the invention, the wall thickness of the outer layer 24 may be about 0.006 inches to 0.007 inches. Additionally, the aggregate wall thickness of the catheter 20 with all of the catheter layers 21, 23, 24 may be about 0.012 inches to 0.013 inches.

Figure 3A:
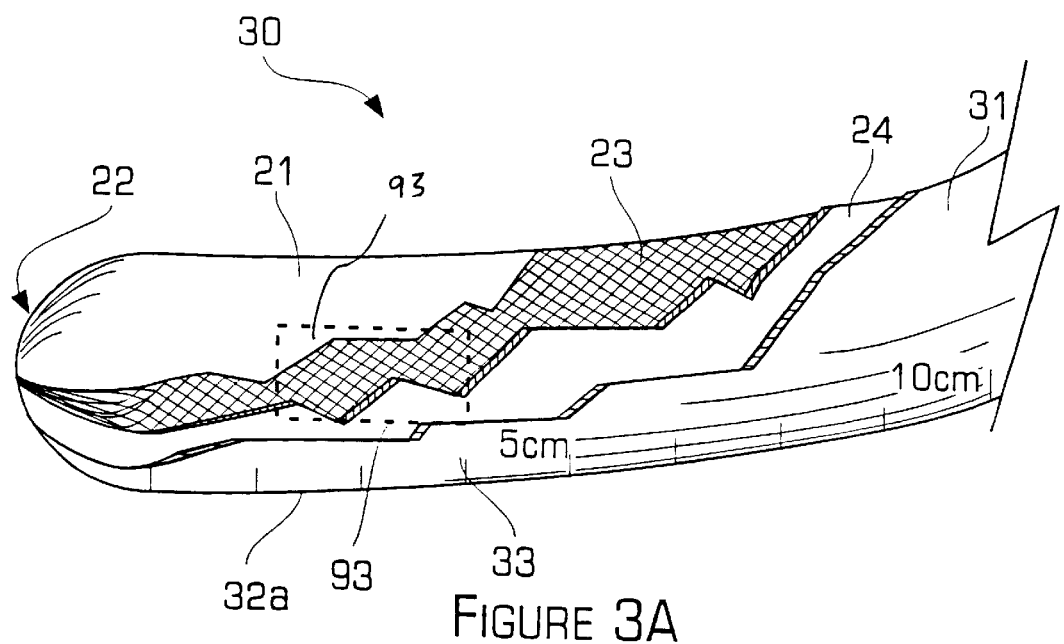
FIGS. 3A and 3B are diagrams of another embodiment of a catheter according to the invention.
Figure 3B:
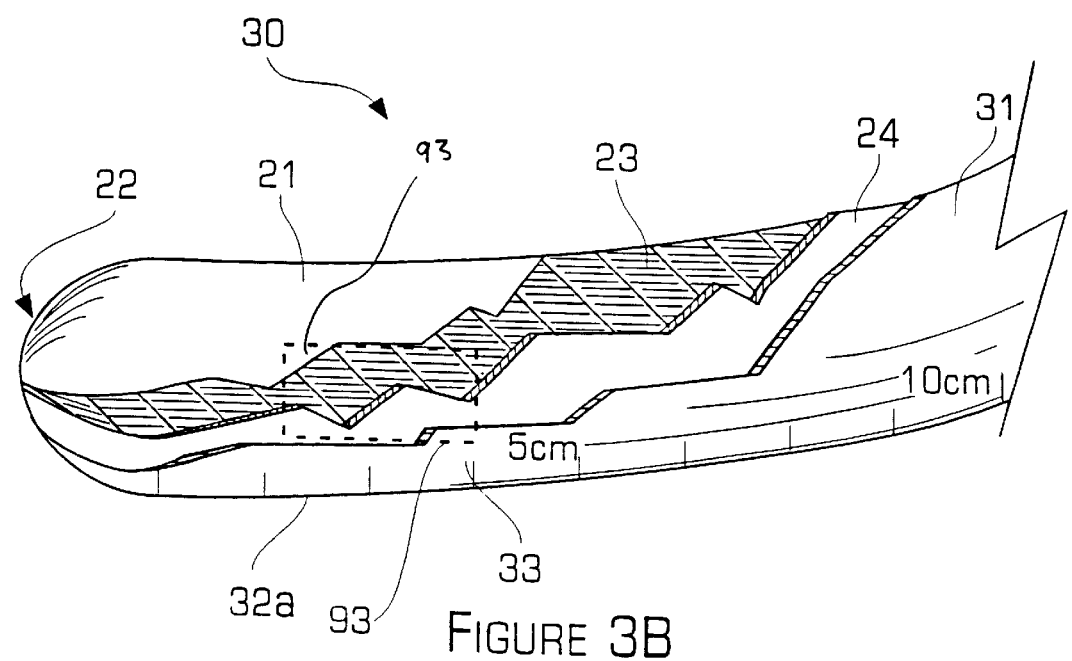

In an alternative embodiment, shown in FIGS. 3A and 3B, in which like elements are represented by like reference numbers, an overcoat layer 31 may be provided that covers the outer layer 24. The fourth overcoat layer may comprise an X-ray detectable material so that the catheter 20 may be tracked within a patient's body during a surgical procedure using X-rays. Preferably, the X-ray detectable material may be a barium-impregnated silicone material, or just a silicone material. Additionally, a distal end 32a of the overcoat layer 31 may be marked on its outer surface 33 with length/depth information, (e.g., 1-cm differential increments) so that a position (depth) of the catheter body 20 in a patient may be determined quickly.

During insertion of the catheter 20 into a patient, the catheter 20 may be inserted with a wire guide, such as a stylet (not shown). The wire guide, or stylet, may help to maintain the catheter 20 in a fixed position so that the catheter 20 may be completely inserted within the patient. The catheter 20 may then be positioned within the patient at which time the wire guide may be removed from the patient leaving only the catheter 20 within the patient. After removal of the wire guide, or stylet, a source wire (not shown) may fit within the catheter 20 and may be inserted into the catheter 20 by a computer-controlled remote afterloader system (not shown). The source wire (not shown) may include a guide wire and a neutron source capsule that may be attached to the end of the guide wire. The neutron source capsule may contain the neutron generating material, such as $^{252}$Cf. Source wires and radiation sources are described in detail in previously incorporated co-pending U.S. patent application Ser. Nos. 09/394,234 and 09/395,324.

Figure 4A:
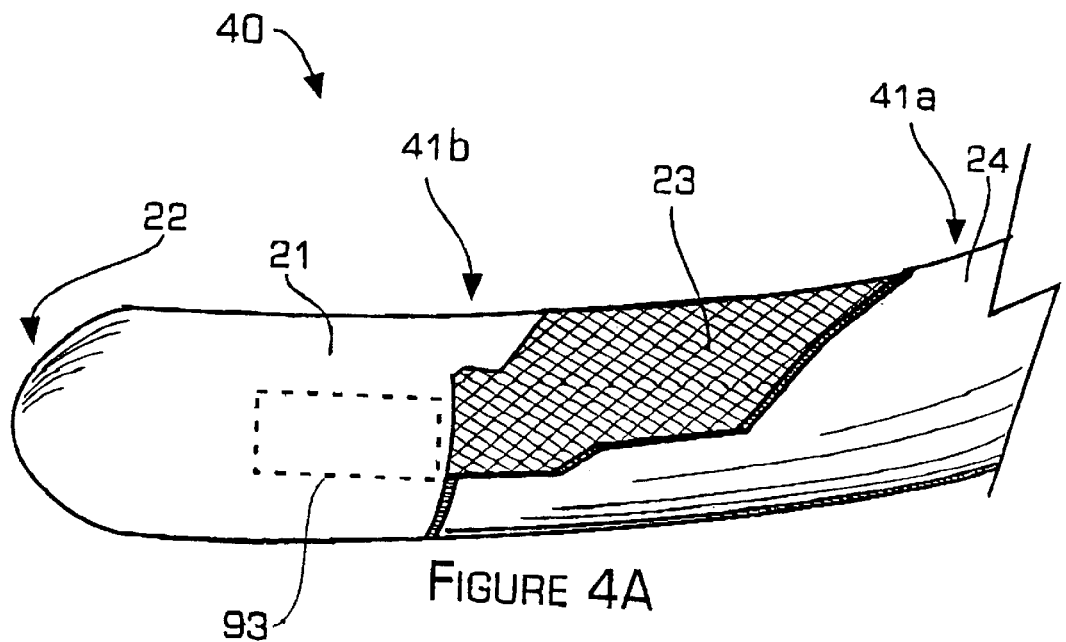
FIGS. 4A and 4B are diagrams of yet another embodiment of a catheter according to the invention.
Figure 4B:
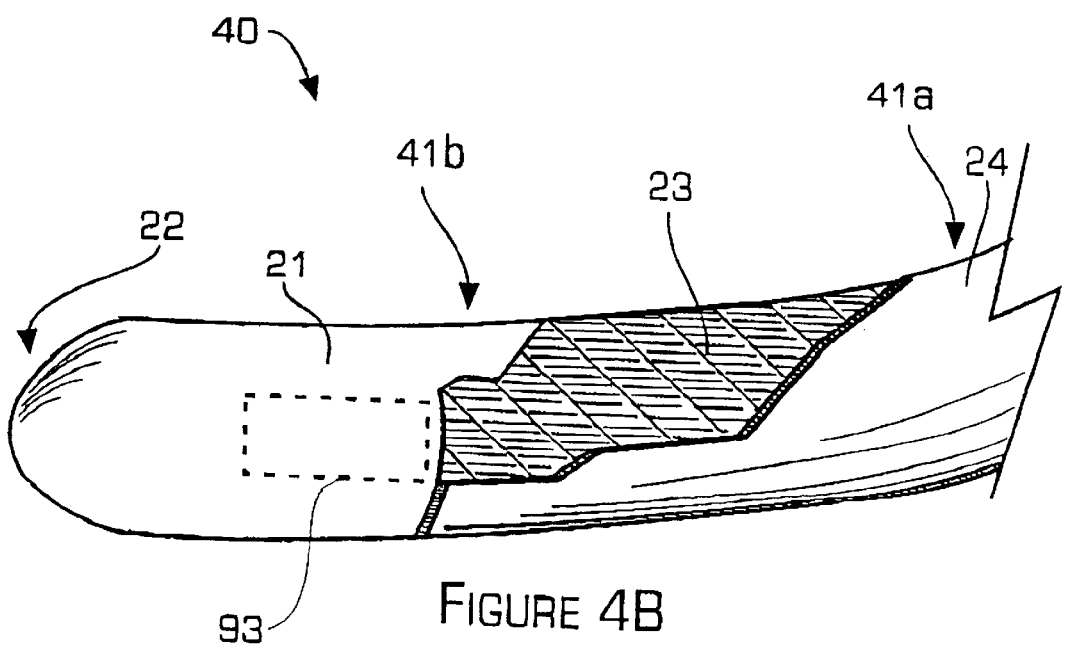

FIGS. 4A and 4B illustrate another embodiment of a reinforced catheter 40 in accordance with the invention. In FIGS. 4A and 4B, like elements are represented by like reference numbers. In this alternative embodiment, the reinforcing layer 23 may not overlay and cover the distal end 20a of the catheter end 22 of the catheter body 40. Certain radiation sources, such as x-ray, gamma and beta and sources, may be affected by the presence of metal around the tip of the catheter 40. This embodiment solves that problem while maintaining the other advantageous properties of the invention. In the case of Californium being used as a brachytherapy source, metal reinforced catheters may be utilized because neutrons emitted from $^{252}$Cf are not attenuated by the metal.

Thus, in this embodiment, the reinforcing layer 23 does not extend over the distal end 20a of the catheter body 40 where a radiation source 93 may be located. Instead, the reinforcing layer 23 may extend adjacent the tip end 22 so that it does not overlay the tip end 22. The distance from the tip end 22 to the edge of the reinforcing layer 23 can be as much as 20 cm for example, or it could be only a few centimeters from the tip end 22, depending on the type of radiation source and the design of the device. Since no metal is covering the radiation source 93, the reinforcing layer 23 will not attenuate the radiation from the source and a patient may receive a full dose of treatment. The actual length of this unbraided or non-coiled segment can vary between manufacturers in order to accommodate different brachytherapy treatment plans.

In this embodiment, the outer layer 24 may overlay the reinforcing layer 23 and the inner layer 21 such that the outer layer 24 extends over the distal end 20a to seal the catheter body 40 as described above. Thus, a first portion 41a of the catheter body 40 may be characterized by a first thickness formed of the thicknesses of the inner, middle and outer layers 21, 23, 24 and a second portion 41b of the catheter body 40 may be characterized by a second thickness formed of the thicknesses of the inner and outer layers 21, 24 only. As with other embodiments, an overcoat layer 31 (not shown in the Figure) may overlay the outer layer 24.

Figure 5:
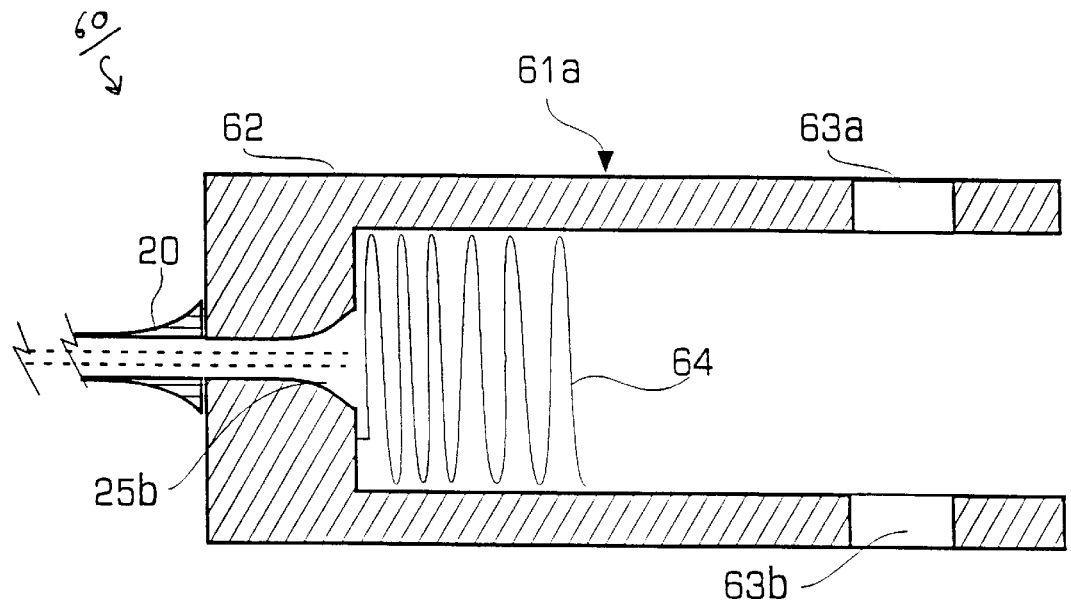
FIG. 5 is a diagram showing the connection of a catheter to a catheter connector in accordance with the invention.

A connector in accordance with the invention may operate to connect a catheter 20 to a piece of extension tubing or directly to a remote afterloader for inserting a radiation source into the catheter 20. FIG. 5 shows an end 25b of the catheter body 20 connected to a connector 60 in accordance with the invention. Preferably, the end 25b of the catheter 20 may be flared to form a funnel shape. This shape may provide strain relief and accommodate any misalignment that might occur for the catheter body 20 when it is connected with another connector 60. While the end 25b is shown as flared, it should be understood that alternative configurations which provide stress relief may be possible without departing from the invention.

FIG. 6A shows an embodiment of a connector 60 according to the invention. A connector 60 may comprise two halves 61a, 61b. The first half 61a may include a housing 62 having at least one pair of opposing cutout portions 63a, 63b of a first depth provided therein. A biasing spring 64 may also be provided within the housing 62. The biasing spring 64 may operate to secure the first half 61a and the second half 61b together when the two halves 61a, 61b are mated by providing a spring force that presses the second half 61b of the connector 60 against the first half 61a. Other biasing elements that may secure the two halves 61a, 61b maybe utilized without departing from the invention.

The second half 61b of the connector 60 may include an inner member 65a and an outer member 65b. The outer member 65b may be configured to slide relative to the inner member 65a. At least one pair of opposing tab portions 66a, 66b may be provided on the inner member 65a. The tab portions 66a, 66b may protrude through the outer member 65b such that when the first half 61a and the second half 61b of the connector 60 are mated, the tab portions 66a, 66b may engage respective cutout portions 63a, 63b of the first half 61a to secure the first half 61a and the second half 61b in combination with the spring 64 that operates to push the tab portions 66a, 66b against the cutout portions 63a, 63b via the spring force. Preferably, the tab portions 66a, 66b may be shorter than the depth of the cutout portions 63a, 63b so that the tab portions 66a, 66b do not protrude beyond the cutout portions and cannot be accidentally disengaged. The tab portions 66a, 66b can be formed by machining away material from a solid body, such as the second half 61a of the connector 61. Machining away material from the body causes the tab portions 66a, 66b to be free to compress and rebound on their own. Alternatively, the tab portions 66a, 66b can be formed as relieved portions with respect to the body. The tab portions 66a, 66b are thereby free to compress and rebound on their own.

When mated, the first half 61a and the second half 61b may be slidably locked via the tab/cutout engagement 63a, 66a, 63b, 66b. In contrast with conventional catheters in which a standard Leur lock may become disengaged due to rotational movement of the catheter within a patient's body, the catheter 20 and connector 50 of the present invention will be unlikely to become disengaged during an operation. The problems associated with conventional catheter connectors, such as the standard Leur lock connector, in that the rotation required to lock the connector may result in catheter movement within the patient, is solved by the present catheter in that no rotation is required to lock the catheter connector and therefore the catheter will not move within the patient. Thus, a more reliable connector may be utilized without presenting possibility of injury to the patient.

In disengaging the two halves 61a, 61b, the outer member 65b of the second half 61b may be compressed against the biasing means and slid towards the first half 61a of the connector 60. This motion may cause the spring 64 to become compressed inwardly thereby relieving the engaging forces of the tab portions 66a, 66b against the cutout portions 63a, 63b caused by the spring. In such case, the tab portions 66a, 66b may compress and the second half 61b may be slidably removed from the first half 61a.

Figure 6C:
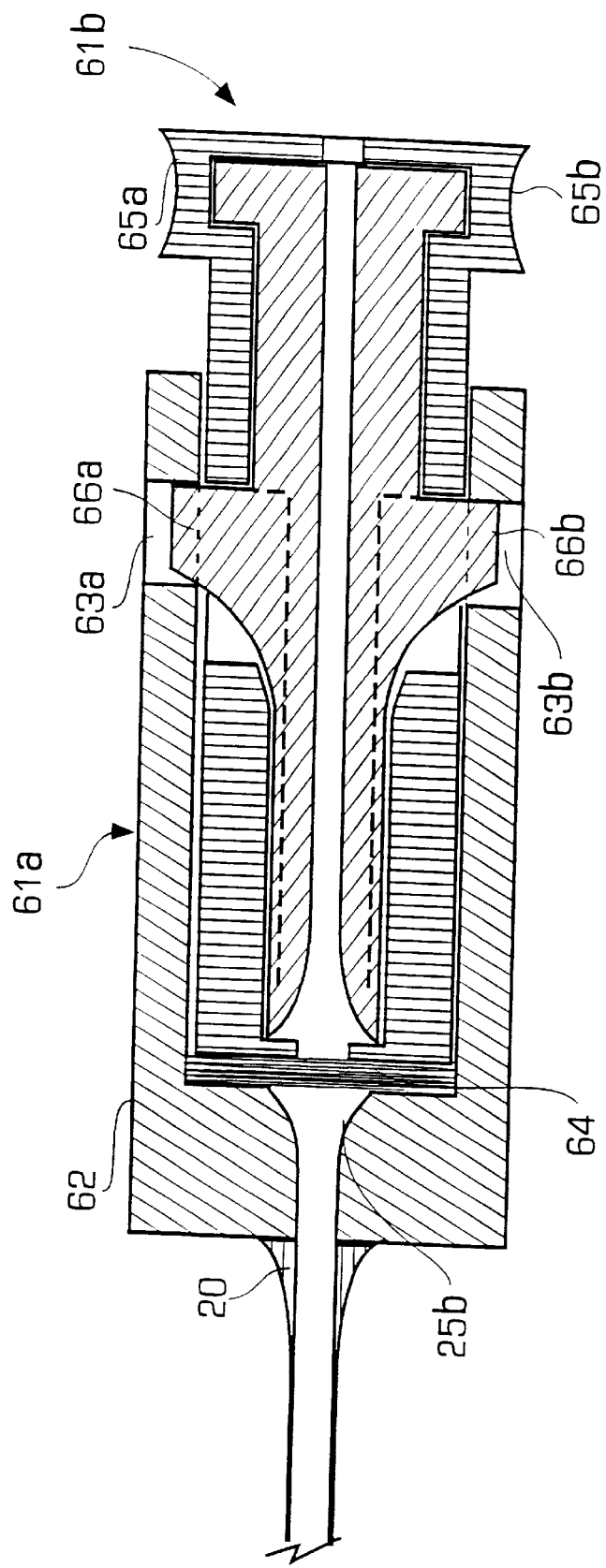
FIG. 6C is a diagram of the catheter connector of FIG. 6A showing the slidable member being engaged with the connector housing to slidably lock the connector in accordance with the invention.

FIGS. 6A–6C show the orientation of a first and second half 61a, 61b of a connector 60 in different relative positions, such as what may occur during mating of the two halves 61a, 61b. In the Figures, like elements are represented by like reference numerals. In FIG. 6A, the first half 61a and the second half 61b are disposed adjacent each other, but not mated, such as what may occur initially during connection of the two halves 61a, 61b. In FIG. 6B, the second half 61b is initially inserted within the housing 62. As shown, the housing 62 may be configured to be slightly wider than the outer member 65b such that the outer member 65b may be slidably insertable within the housing 62, resulting in a tight fit. When an outer portion 81 of the tabs 66a, 66b contact the housing 62, the tab portions 66a, 66b may compress such that the outer member 65b may continue to be slidably inserted within the housing 62.

In FIG. 6C, the second half 61b is completely inserted within the housing 62. As shown, the tab portions 66a, 66b engage respective cutout portions 63a, 63b to secure the two halves 61a, 61b of the connector 60. The biasing spring 64 provides a translational force against the second half 61b such that the tab portions 66a, 66b are pressed against the inner surface 82 of the respective cutout portions 63a, 63b. Therefore, it is unlikely that the two halves 61a, 61b may become disengaged due to positional changes of the catheter connector 60. Due to the close fitting relationship between the housing 62 and the outer member 65b, the catheter body 20 may be oriented such that tight tolerances are maintained with a catheter body 20 disposed within the second half 61b.

Figure 7A:
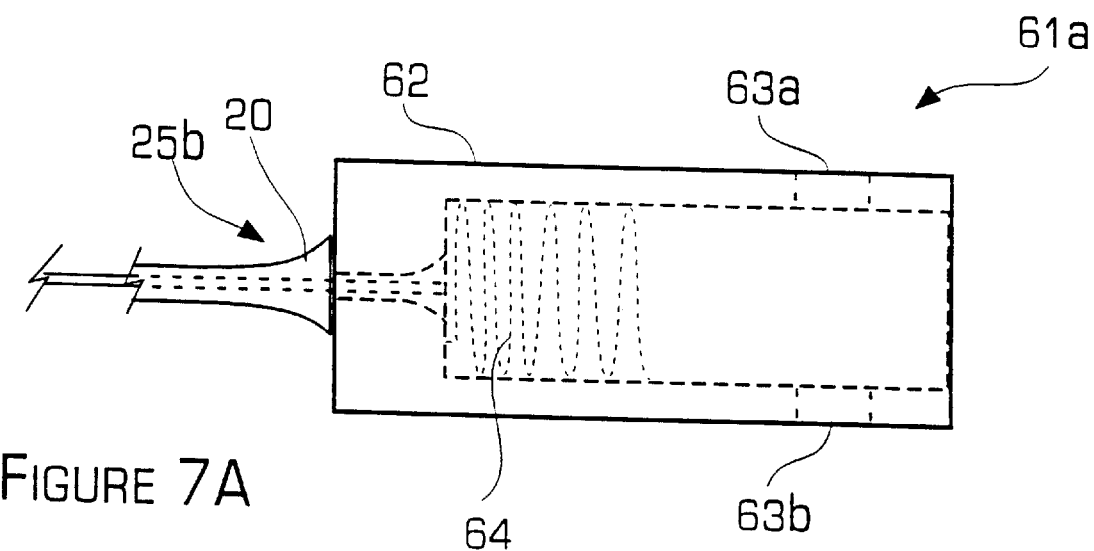
FIG. 7A is a diagram of the connector housing portion of the catheter connector shown in FIGS. 6A–6C.
Figure 7B:
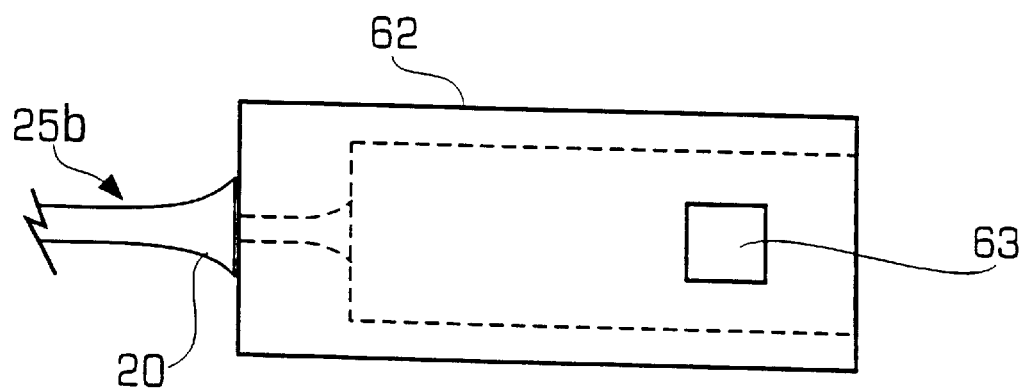
FIG. 7B is a side view of the housing of FIG. 7A.
Figure 7C:
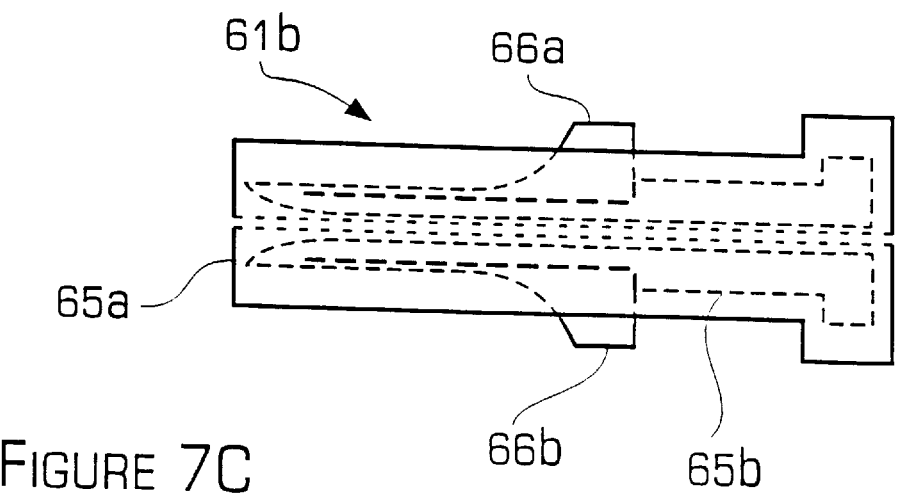
FIG. 7C is a diagram of the slidable connector portion of the catheter connector shown in FIGS. 6A–6C.

FIGS. 7A–7C show embodiments of the first half 61a and second half 61b of the connector 60, respectively. Preferably, the tab portions 66a, 66b may be configured in a "wing" shape having an angled edge. Alternatively, a rounded shape or more angular shape may be utilized without departing from the invention. Preferably, though, the tab portions 66a, 66b may be configured such that they do not protrude beyond the depth of a cutout portion 63a, 63b in a housing 62 of a connector 60 so that the tab portions 66a, 66b do not protrude beyond the cutout portions 63a, 63b and cannot be accidentally disengaged.

Figure 8:
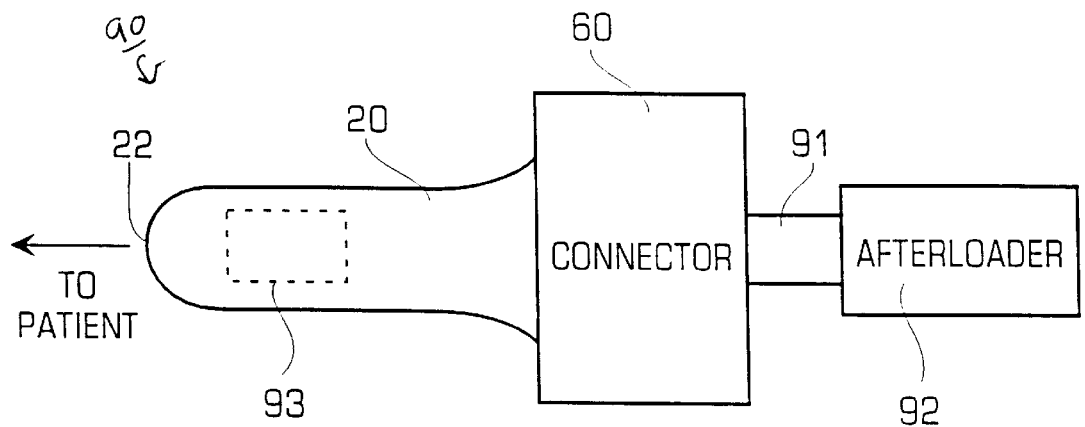
FIG. 8 is a diagram of a catheter system in accordance with the invention.

In operation, such as during a brachytherapy procedure, a catheter system according to the invention may be utilized. An embodiment of a catheter system is shown in FIG. 8. The catheter system 90 may include a catheter body 20 formed of an inner layer 21. The inner layer 21 may have one end that is closed to form a tip end 22. The tip end 22 may be closed and sealed by a middle layer 23. The middle layer 23 may be of either metallic or non-metallic material. The tip end 22 may be configured to house a radiation source 93. The inner layer 21 may be characterized by a low friction coefficient and may be made of a material with that characteristic such as plastic, or polytetrafluoroethylene (PTFE).

The middle layer 23 may be overlaid on the inner layer 21 to aid in reducing the occurrence of kinking of the catheter 20. The middle layer 23 may include a braided or coiled reinforcing structure that may extend entirely over the inner layer 21 so as to overlay the tip end 22. The middle layer 23 may be made of a strong, resilient material such as metal, stainless steel, or a non-metallic material such as nylon. As described above, the middle layer 23 may comprise strands, such as round wires tightly braided around the inner layer 21 or it may include a rectangular cross-sectional wire tightly coiled around the inner layer 21. An outer layer 24 may be overlaid on the middle layer 23 so as to seal the catheter body 20.

The catheter system 90 may additionally include a connector 60 for coupling catheter and extension tubing ends. The catheter end connected with the connector 60 may be flared to form a funnel shape so as to provide the catheter body 20 with strain relief and minimize mismatch of the mating lumens. A connector 60 suitable for use in the catheter system 90 may be such as described above.

The catheter system 90 may also include extension tubing 91 connected with an end of the connector 60 such that an afterloader 92 may be connected with the catheter system. The afterloader 92 may load a radiation source 93 into the catheter system 90.

Alternatively, the middle layer 23 may not extend entirely over the inner layer 21, such that the tip end 22 is not overlaid by the middle layer 23. An outer layer 24 may be overlaid over the middle layer 23 and the tip end 22 such that the catheter body 20 may be sealed. The outer layer 24 may be of a material such as plastic, nylon or polyurethane, such that the outer layer 24 may seal the catheter body 20 and provide a low friction, lubricous coating that may be easily inserted into a patient's body during a surgical procedure such as brachytherapy. Since the outer layer 24 completely overlays the tip end 22, a first portion of the catheter body 20 may be characterized by a first thickness formed of the inner, middle and outer layers 21, 23, 24 and a second portion of the catheter body 20 may be characterized by a second thickness formed of the inner and outer layers 21, 24. This catheter body may be configured to be connected with an afterloader 92 via extension tubing 91 coupled with the connector 60.

While the foregoing has been described with reference to particular embodiments of the invention, it will be appreciated by those skilled in the art that changes in these embodiments may be made without departing from the principles and spirit of the invention, the scope of which is defined by the appended claims. For example, alternative embodiments of the invention may provide for connectors that include additional connecting tabs and other features that cooperate to connect additional connectors and catheters.

What is claimed is:

1. A reinforced catheter, comprising:
   an inner layer forming a catheter body for holding a neutron source capsule, said body having a distal end and a proximal end, said distal end having a closed tip end;
   a middle reinforcing layer extending over said first inner layer to said distal end, the middle reinforcing layer cooperating with the inner layer to reduce the kinking of the inner layer, wherein the middle reinforcing layer has a closed tip end; and
   an outer layer extending over said middle reinforcing layer to seal the reinforced catheter body and to provide a surface coating for the catheter so that the catheter is capable of being easily guided into a patient.

2. A method for performing a surgical procedure on a patient, comprising:
   inserting a reinforced catheter into the body of the patient, the reinforced catheter including:
      an inner layer forming a catheter body for holding a neutron source capsule, said body having a distal end and a proximal end, said distal end having a closed tip end;
      a middle reinforcing layer extending over said first inner layer to said distal end, wherein the middle reinforcing layer has a closed tip end; and
      an outer layer extending over said middle reinforcing layer.

3. A reinforced catheter, comprising:
   an inner layer forming a catheter body, said body having a distal end and a proximal end, said distal end having a closed tip end;
   a middle reinforcing layer extending over said first inner layer to said distal end, said middle reinforcing layer comprising braided non-metallic strands, wherein the middle reinforcing layer has a closed tip end; and
   an outer layer extending over said middle reinforcing layer.

4. A reinforced catheter, comprising:
   an inner layer forming a catheter body, said body having a distal end and a proximal end, said distal end having a closed tip end;
   a middle reinforcing layer extending over said first inner layer to said distal end, said middle reinforcing layer comprising braided non-metallic strands and cooperating with the inner layer to reduce the kinking of the inner layer, wherein the middle reinforcing layer has a closed tip end; and
   an outer layer extending over said middle reinforcing layer to seal the reinforced catheter body and to provide a surface coating for the catheter so that the catheter is capable of being easily guided into a patient.

* * * * *